US00PP13670P29

(12) United States Plant Patent
Lamb et al.

(10) Patent No.: US PP13,670 P2
(45) Date of Patent: Mar. 18, 2003

(54) SPATHIPHYLLUM PLANT NAMED 'VALENTINO'

(75) Inventors: Ann Elizabeth Lamb, Sebring, FL (US); David R. Lilly, Boynton Beach, FL (US)

(73) Assignee: Twyford International Inc., Santa Paula, CA (US)

( * ) Notice: Subject to any disclaimer, the term of this patent is extended or adjusted under 35 U.S.C. 154(b) by 0 days.

(21) Appl. No.: 10/142,841

(22) Filed: May 10, 2002

(51) Int. Cl.[7] ..... A01H 5/00

(52) U.S. Cl. ..... Plt./364

(58) Field of Search ..... Plt./364

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Spathiphyllum plant named 'Valentino', characterized by its upright, somewhat outwardly arching and symmetrical plant habit; glossy dark green leaves; rapid growth rate; freely flowering habit; white-colored spathes that are positioned well above the foliage on erect peduncles; and good postproduction longevity.

4 Drawing Sheets

BOTANICAL CLASSIFICATION/CULTIVAR DESIGNATION

Spathiphyllum hybrid cultivar Valentino.

BACKGROUND OF THE INVENTION

The present Invention relates to a new and distinct cultivar of Spathiphyllum plant, botanically known as Spathiphyllum hybrid, and hereinafter referred to by the cultivar name Valentino The new cultivar is a product of a planned and controlled breeding program conducted by the Inventors in Apopka, Fla. The objective of the breeding program is to create new Spathiphyllum cultivars with improved plant habit, dark green foliage and rapid growth rate.

The new cultivar originated from a cross-pollination made by the Inventors on Feb. 9, 1998 of the Spathiphyllum hybrid cultivar Sparkle, disclosed in U.S. Plant Pat. No. 8,367, as the female or seed parent and the Spathiphyllum hybrid cultivar 31581, disclosed in U.S. Plant Pat. No. 10,893, as the male or pollen parent. The cultivar Valentino was discovered and selected by the Inventors as a plant within the progeny of the stated cross-pollination in a controlled environment in Homestead, Fla., on Sep. 23, 1999.

Asexual propagation of the new cultivar by tissue culture since September, 1999, in a laboratory in Sebring, Fla., has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature and light intensity, without, however, any variance in genotype.

The following traits have been repeatedly observed and are determined to be the unique characteristics of 'Valentino'. These characteristics in combination distinguish 'Valentino' as a new and distinct Spathiphyllum cultivar:

1. Upright, somewhat outwardly arching and symmetrical plant habit.

2. Glossy dark green leaves with undulate leaf margins.

3. Rapid growth rate.

4. Freely flowering habit.

5. White-colored spathes that are positioned well above the foliage on erect peduncles.

6. Good postproduction longevity.

Plants of the new Spathiphyllum differed from plants of the female parent, the cultivar Sparkle, when grown in side-by-side comparisons in Apopka, Fla., in the following characteristics:

1. Plants of the new Spathiphyllum were smaller than plants of the cultivar Sparkle.

2. Plants of the new Spathiphyllum were more freely clumping than plants of the cultivar Sparkle.

3. Spathes of plants of the new Spathiphyllum were smaller than spathes of plants of the cultivar Sparkle.

4. Spathes of plants of the new Spathiphyllum were ovate in shape whereas spathes of plants of the cultivar Sparkle were elliptic in shape.

Plants of the new Spathiphyllum differed from plants of the male parent, the cultivar 31581, when grown in side-by-side comparisons in Apopka, Fla., in the following characteristics:

1. Plants of the new Spathiphyllum grew faster than plants of the cultivar 31581;

2. Plants of the new Spathiphyllum were more freely flowering than plants of the cultivar 31581.

Plants of the new Spathiphyllum can be compared to plants of the Spathiphyllum cultivar Petite, not patented. In side-by-side comparisons conducted in Apopka, Fla., plants of the new Spathiphyllum differed from plants of the cultivar Petite in the following characteristics:

1. Leaves of plants of the new Spathiphyllum were darker green in color and glossier than leaves of plants of the cultivar Petite.

2. Leaves of plants of the new Spathiphyllum had more acute apices than leaves of plants of the cultivar Petite.

3. Plants of the new Spathiphyllum tolerated high temperatures better than plants of the cultivar Petite.

Plants of the new Spathiphyllum can also be compared to plants of the Spathiphyllum cultivar Claudia, disclosed in U.S. Plant Pat. No. 12,547. In side-by-side comparisons conducted in Apopka, Fla., plants of the new Spathiphyllum differed from plants of the cultivar Claudia in the following characteristics:

1. Plants of the new Spathiphyllum were smaller than plants of the cultivar Claudia.

2. Plants of the new Spathiphyllum were more freely clumping than plants of the cultivar Claudia.

3. Leaves of plants of the new Spathiphyllum were smaller, more narrow and glossier than leaves of plants of the cultivar Claudia.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Spathiphyllum.

The photograph on the first sheet comprises a side perspective view of a typical 15-month old plant of 'Valentino' grown in a 20-cm container.

The photograph on the second sheet comprises a close-up view of typical inflorescences of 'Valentino'.

The photograph on the third sheet comprises a close-up view of the upper leaf surface of a typical plant of 'Valentino'.

The photograph on the fourth sheet comprises a close-up view of the lower leaf surface of a typical plant of 'Valentino'.

DETAILED BOTANICAL DESCRIPTION

The aforementioned photographs and following observations, measurements and comparisons describe 15-month old plants (from planting rooted tissue-cultured plantlets) grown during the winter and spring in Homestead, Fla., in a polypropylene-covered shadehouse and under commercial production conditions in 20-cm containers. During the production of the plants, day temperatures ranged from 70 to 90° F., night temperatures ranged from 65 to 75° F., and light levels were about 1,500 to 2,000foot-candles.

In the following description, color references are made to The Royal Horticultural Society Colour Chart, 1995 Edition, except where general terms of ordinary dictionary significance are used.

Botanical classification: Spathiphyllum hybrid cultivar Valentino.

Parentage:

*Female parent.*—Spathiphyllum hybrid cultivar Sparkle, disclosed in U.S. Plant Pat. No. 8,367.

*Male parent.*—Spathiphyllum hybrid cultivar 31581, disclosed in U.S. Plant Pat. No. 10,893.

Propagation:

*Type.*—By tissue culture.

*Time to initiate roots on a tissue-cultured cutting.*—Summer: About 6 to 8 days at 70 to 90° F. day temperature and 65 to 75° F. night temperature. Winter: About 7 to 10 days at 70 to 90° F. day temperature and 65 to 75° F. night temperature.

*Time to produce a fully-rooted tissue-cultured plantlet.*—Summer: About 70 days at 70 to 90° F. day temperature and 65 to 75° F. night temperature. Winter: About 84 days at 70 to 90° F. day temperature and 65 to 75° F. night temperature.

*Root description.*—Thick, fleshy; lateral branch roots, fine; white in color.

*Rooting habit.*—Freely branching.

Plant description:

*Plant shape.*—Upright, somewhat outwardly arching and symmetrical plant habit; small to intermediate in stature.

*Growth habit.*—Erect when young, becoming somewhat outwardly arching as leaves develop. Freely clumping and full appearance; about 16 clumps per plant. Plants of the new Spathiphyllum are typically grown in 15 to 20-cm containers.

*Plant height.*—About 30 to 36 cm from soil level to top of leaf plane and about 49 to 62 cm from soil level to spathe apices.

*Plant spread.*—About 70 to 75 cm.

*Growth rate.*—Rapid growth rate; from tissue-cultured plantlets, about 7 to 8 months are required to produce finished flowering plants in 15-cm containers.

*Foliage description.*—Length: About 20 to 26 cm. Width: About 7.5 to 9 cm. Shape: Lanceolate. Apex: Elongated acuminate. Base: Cuneate. Margin: Entire; moderately undulate. Aspect: Initially upright, then somewhat outwardly arching; curved downward at apex. Surface: Rugose; midrib sunken on upper surface and prominent on lower surface. Texture, upper and lower surfaces: Leathery, smooth, glabrous, durable and flexible. Venation pattern: Pinnate. Color: Young and fully expanded leaves, upper surface: Darker and more green than, but closest to 137A; glossy. Young and fully expanded leaves, lower surface: 137C; dull. Midrib, upper surface: 137A. Midrib, lower surface: 146C. Petiole: Length: About 20 to 23 cm. Diameter, just below the geniculum: About 3.5 to 4 cm. Petiole sheath, length: About 15 to 17 cm; about 1 to 2 cm between the petiole sheath apex and the base of the geniculum. Petiole sheath, diameter: About 7 mm. Petiole sheath, apex: Rounded. Geniculum length: About 1.8 to 3.5 cm. Geniculum diameter: About 4 mm. Geniculum aspect: Straight to curved. Color: Petiole and sheath: Darker than, but closest to 137A. Geniculum: 137A to 137B.

Inflorescence description:

*Inflorescence arrangement/quantity*—Concave spathes with spadices held above the foliage on erect peduncles. Freely flowering; typically about 15 developing and open spathes per plant at one time; inflorescences arise from the petiole sheath.

*Time to flower.*—Inflorescences are initiated in the late winter and early spring in Homestead, Fla.

*Inflorescence longevity.*—Spathes generally maintain white color for about four weeks on the plant. As cut flowers, spathes maintain good substance for about seven days.

*Fragrance.*—Slightly fragrant, sweet, typical of Spathiphyllum.

*Inflorescence buds*—Length: About 8 to 9 cm. Diameter: About 7 to 9 mm. Shape: Spindle-shaped. Color: 155A; venation, 144D; towards the apex, 137C to 137D.

*Spathe.*—Length: About 10 to 12 cm. Width: About 4.8 to 6 cm. Depth: About 1.3 cm. Shape: Ovate to elliptic. Apex: Acuminate; twisted. Base: Cuneate. Aspect: Concave, curling over the spadix. Color Front surface: More white than, but closest to 155D; midrib, 155D tinged with 191B. Back surface: More white than, but closest to 155D; midrib, 144A to 146B; apex, 155D tinged with 144A. Front surface with subsequent development: 145C to 146D; midrib, 146B to 146C; apex, 145C to 146A. Back surface with subsequent development: 145A to 145C; midrib, 137A to 146B; apex, 145C to 146A.

*Spadix.*—Length: About 3.2 to 4.5 cm. Diameter: About 1.2 cm. Color: 158C gradually becoming closer to 146C with development. Quantity of flowers: More than 200 per spadix. Pistillate flowers extend about 1.5 mm beyond the staminate flowers. Pollen: Scarce. Pollen color: Close to 155D. Pistils: Conical; close to 155D in color.

*Peduncle.*—Length: About 39 to 52 cm. Diameter: About 3.5 to 4.5 mm. Color: Darker than, but closest to 137A.

*Fruit.*—Type: Berry. Length: About 6 mm. Diameter: About 4 mm. Shape: Oblong to elliptic. Color: Darker than, but closest to 147A; with subsequent development, tinged with 19B to 19C.

*Seed.*—Quantity per fruit: About one to six. Quantity per inflorescence: About 150. Length: About 2 mm. Shape: Reniform. Color: Light brown.

Disease/pest resistance: Plants of the new Spathiphyllum have not been observed to be resistant to pathogens or pests common to Spathiphyllum.

Temperature tolerance: Plants of the new Spathiphyllum have been observed to tolerate temperatures from 45 to 104° F.

It is claimed:

1. A new and distinct cultivar of Spathiphyllum plant named 'Valentino', as illustrated and described.

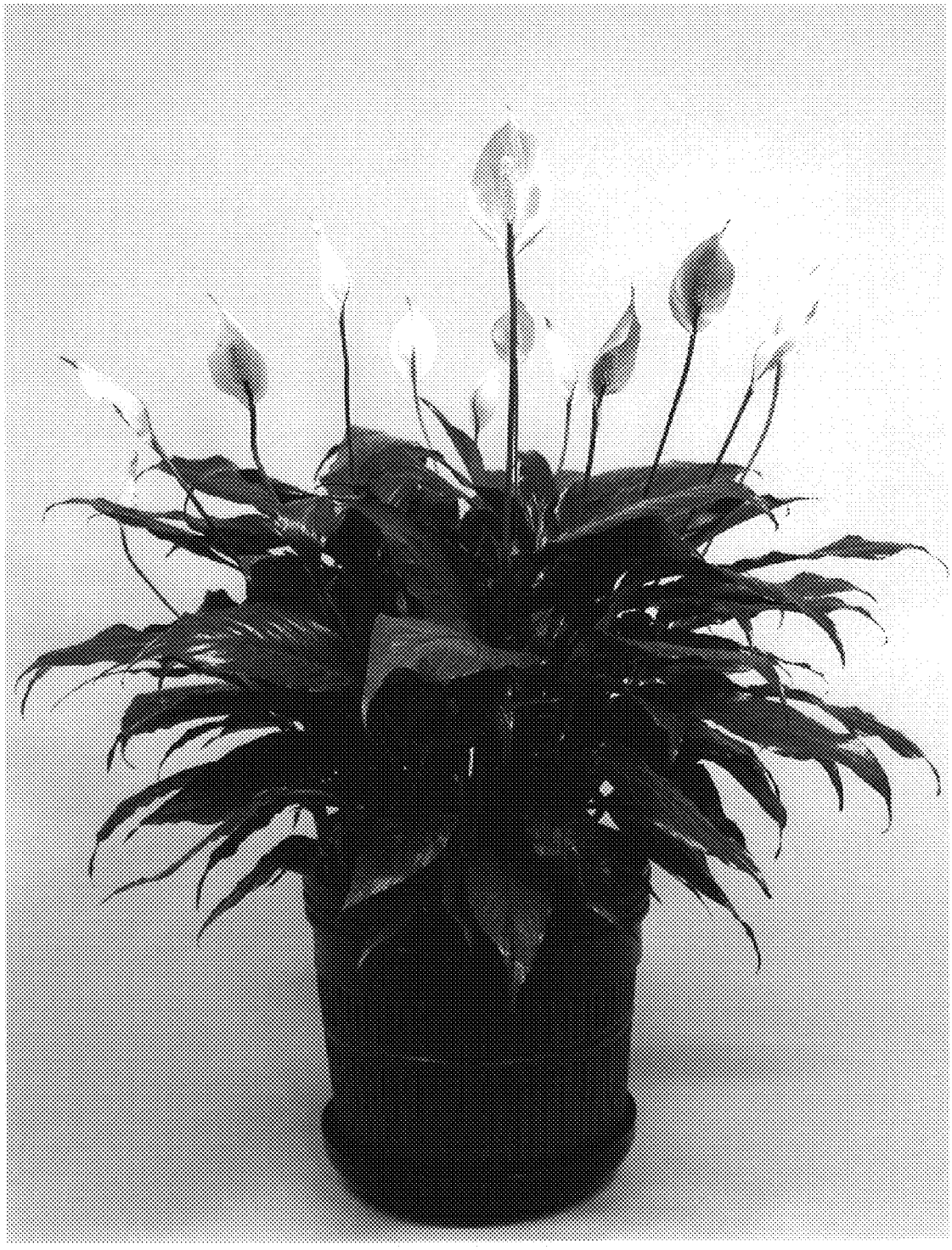

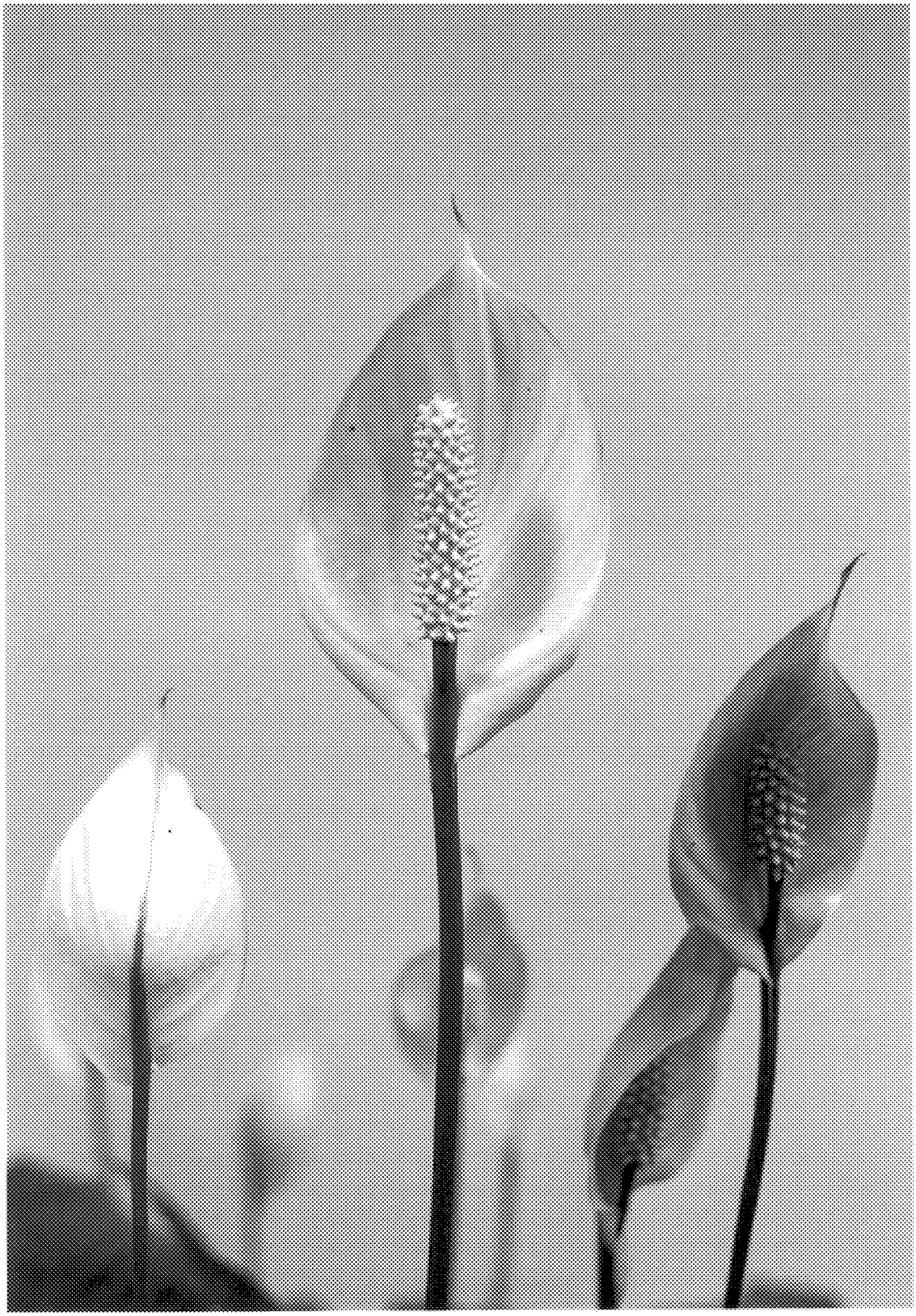

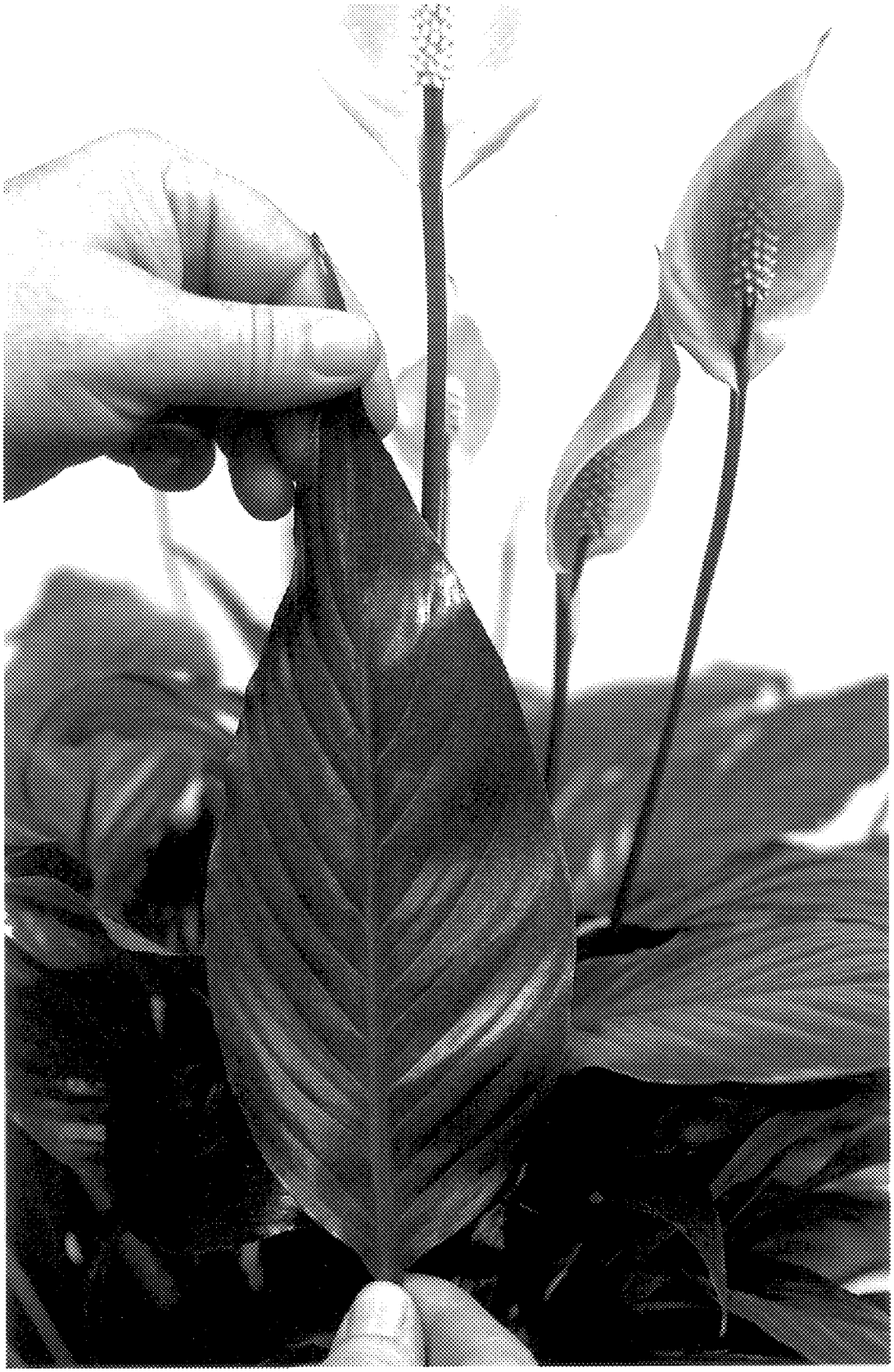

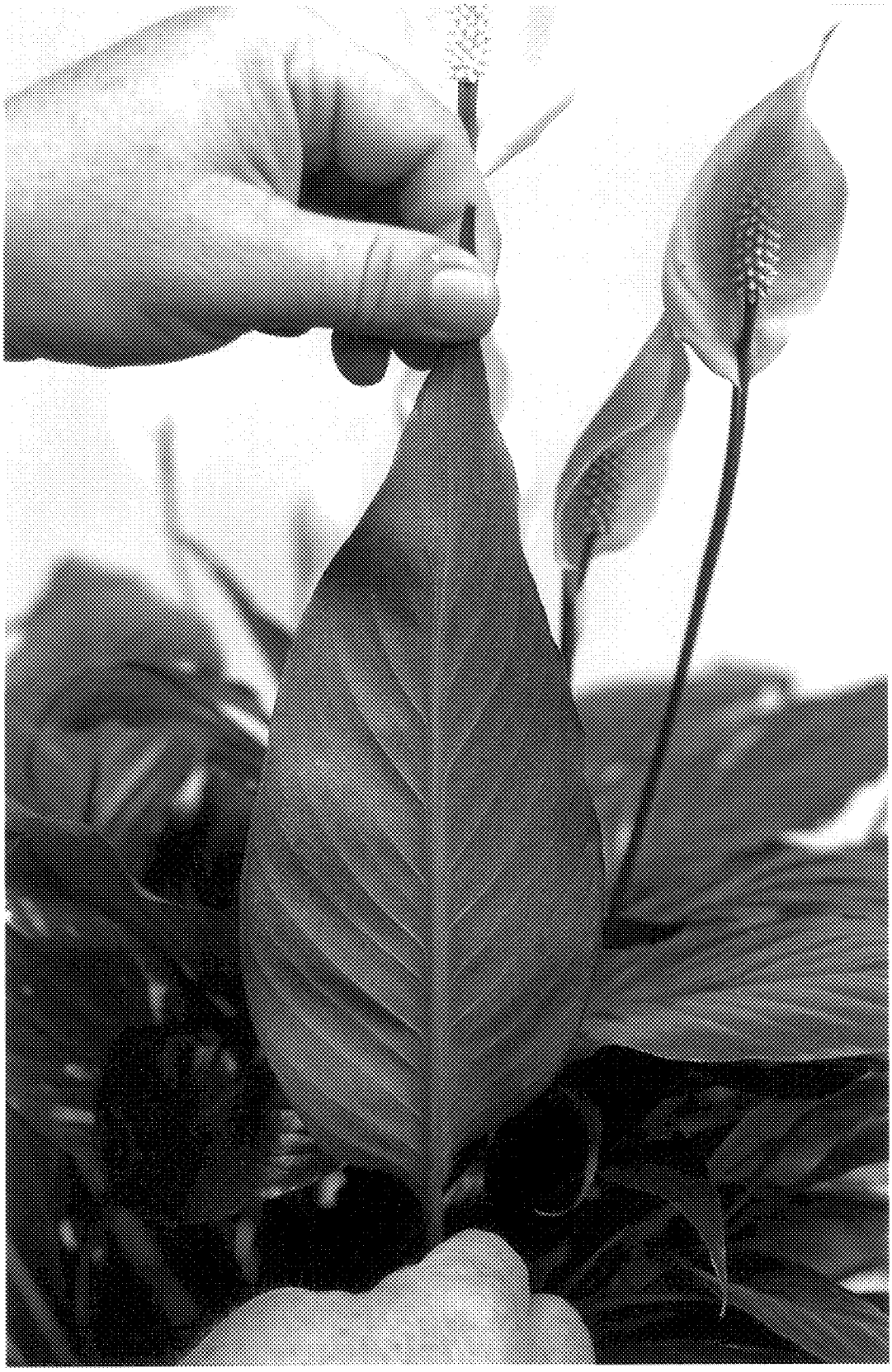

* * * * *